United States Patent

Falwell et al.

[11] Patent Number: 5,944,690
[45] Date of Patent: Aug. 31, 1999

[54] SLIDABLE CONTROL MECHANISM FOR STEERABLE CATHETER

[75] Inventors: Gary S. Falwell, Manchester, N.H.; Sarkis Karakozian, Belmont, Mass.

[73] Assignee: C.R. Bard, Inc., Murry Hill, N.J.

[21] Appl. No.: 08/818,352

[22] Filed: Mar. 17, 1997

[51] Int. Cl.⁶ ................................................. A61M 37/00
[52] U.S. Cl. ............................................. 604/95; 600/146
[58] Field of Search ........................... 604/95, 280, 264; 606/41, 205–208; 600/129, 131, 139, 146, 147

[56] References Cited

U.S. PATENT DOCUMENTS

| | | | |
|---|---|---|---|
| 4,294,233 | 10/1981 | Takahashi . | |
| 4,874,371 | 10/1989 | Comben et al. | 604/95 |
| 5,364,351 | 11/1994 | Heinzelman et al. . | |
| 5,383,852 | 1/1995 | Stevens-Wright | 604/95 |
| 5,527,279 | 6/1996 | Imran | 604/95 |
| 5,531,687 | 7/1996 | Snoke et al. | 604/95 |
| 5,611,777 | 3/1997 | Bowden et al. | 604/95 |
| 5,676,653 | 10/1997 | Taylor et al. | 604/95 |

Primary Examiner—John D. Yasko
Attorney, Agent, or Firm—Darby&Darby

[57] ABSTRACT

A steerable catheter control mechanism for manipulating a pair of catheter control wires comprises a slider mechanism coupled to the proximal ends of the control wires and displaceable along a linear path to place a selected one of said wires in tension without placing the other of said wires in compression.

14 Claims, 3 Drawing Sheets

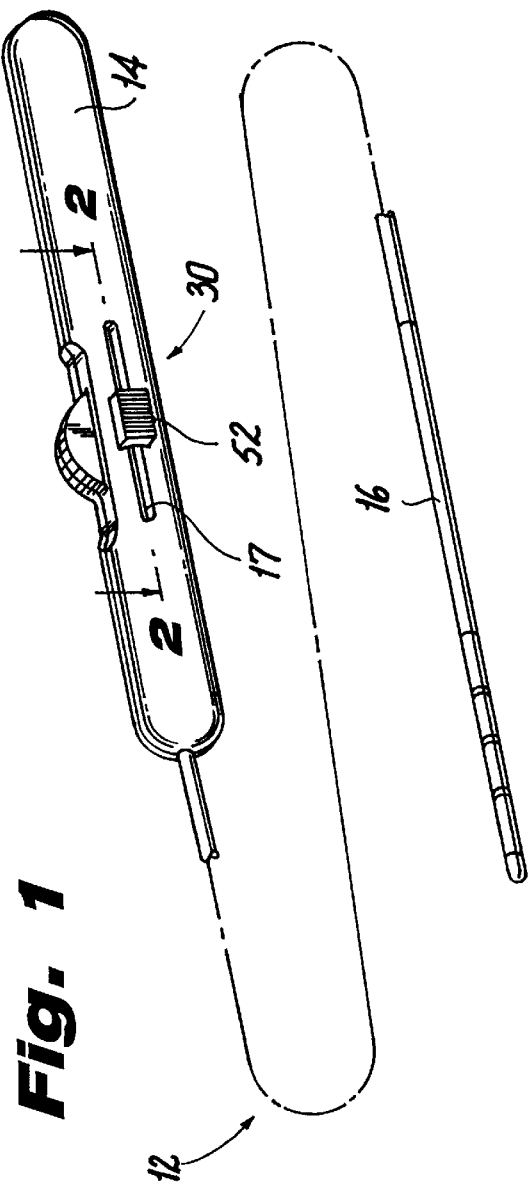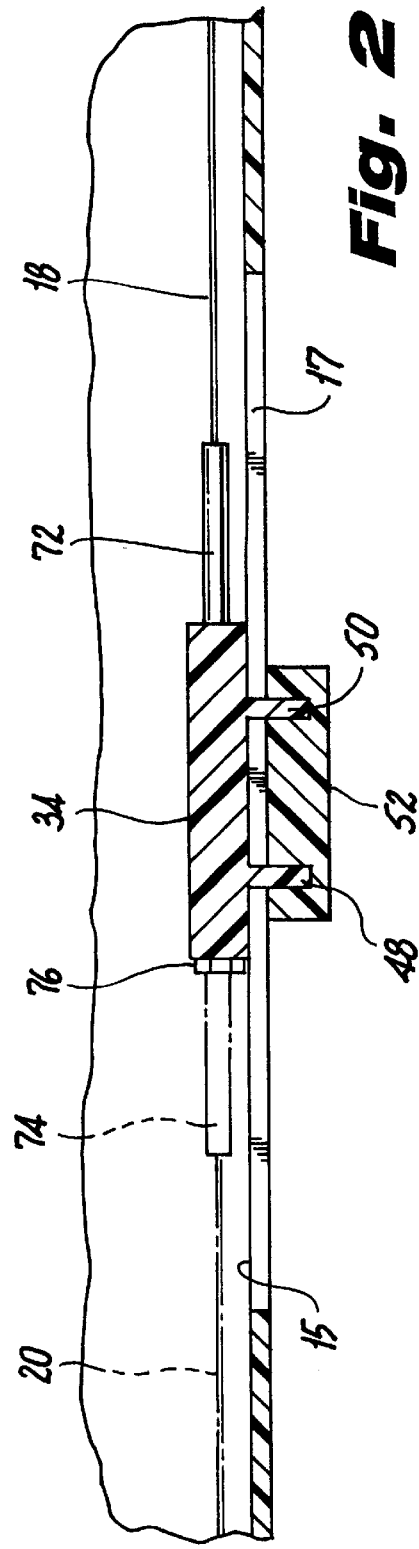

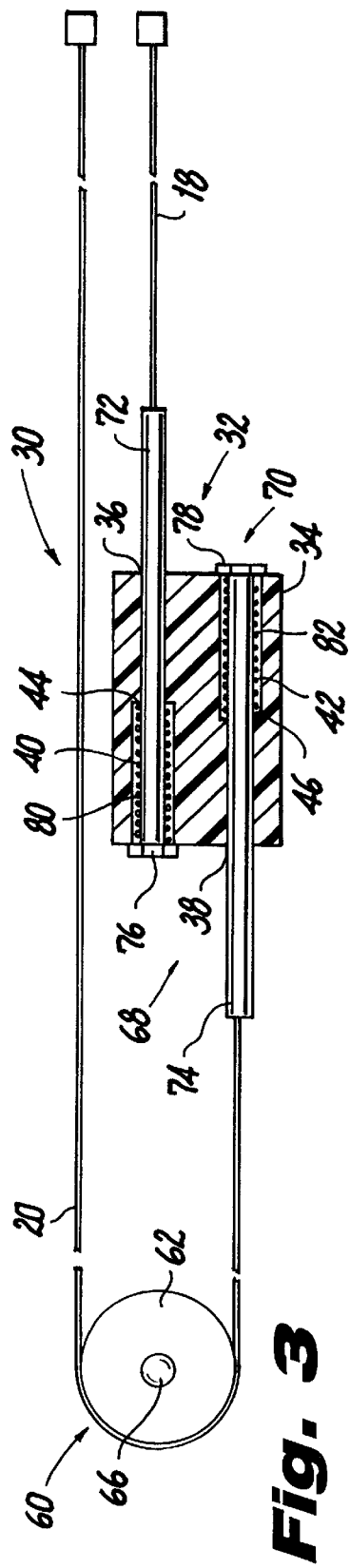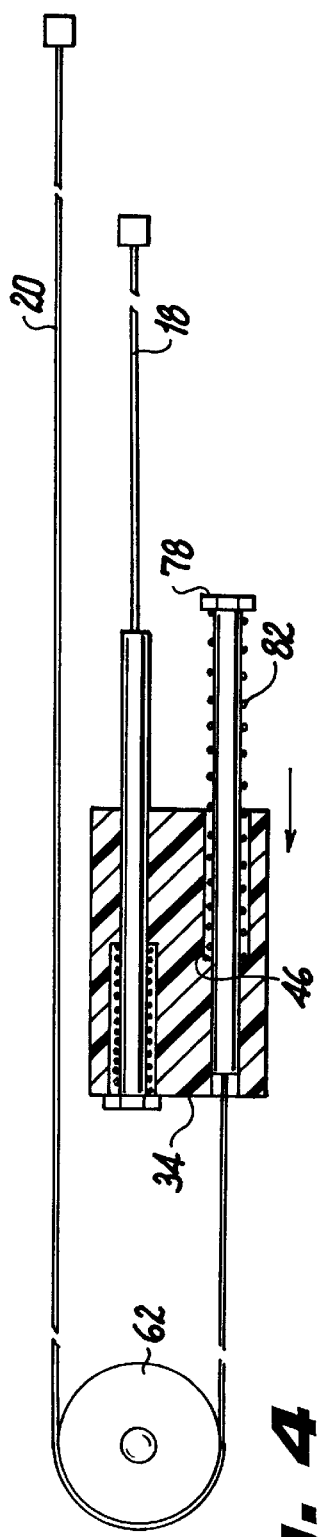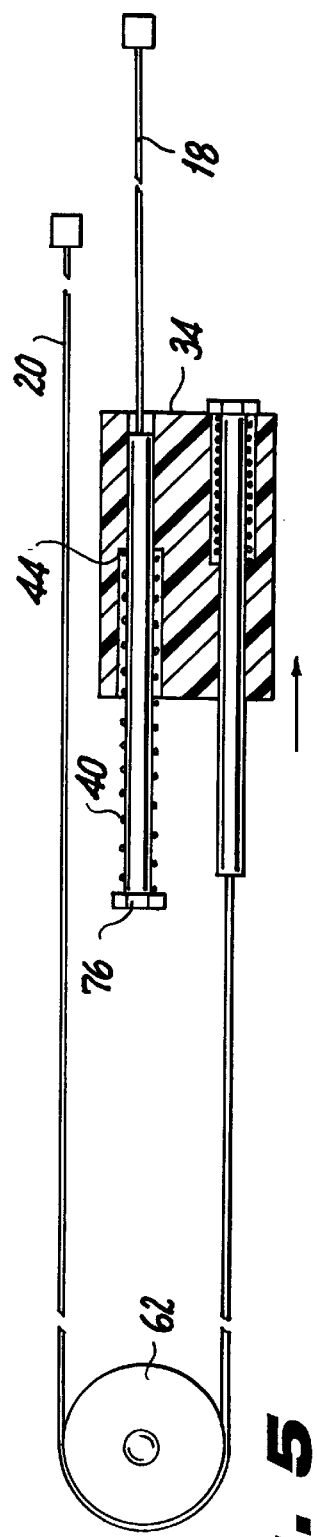

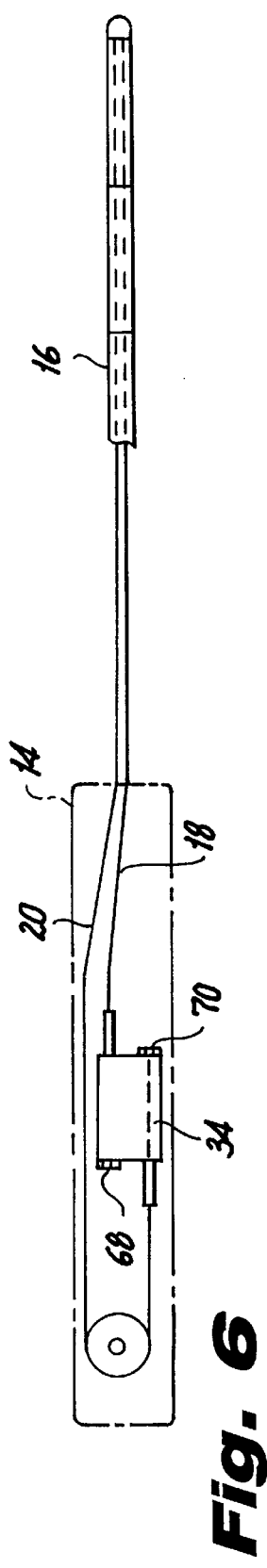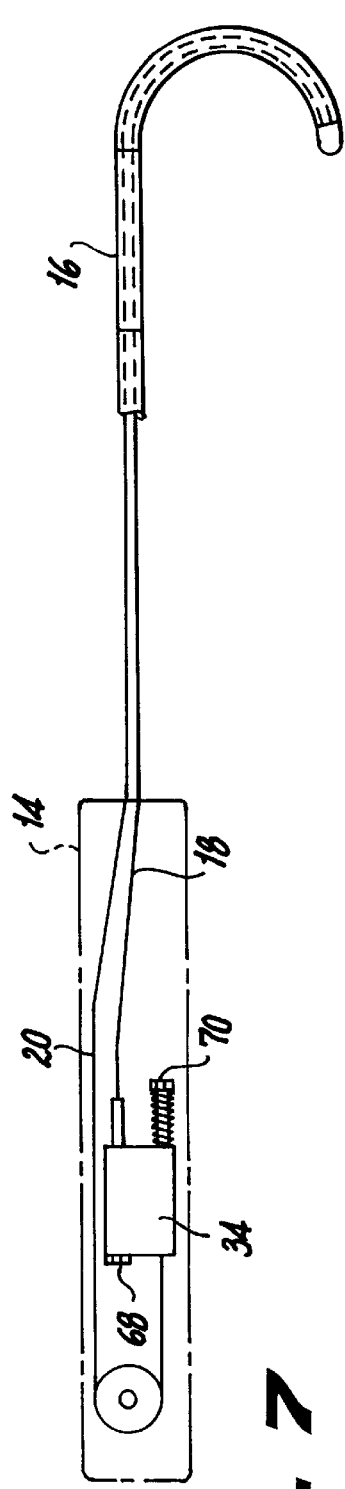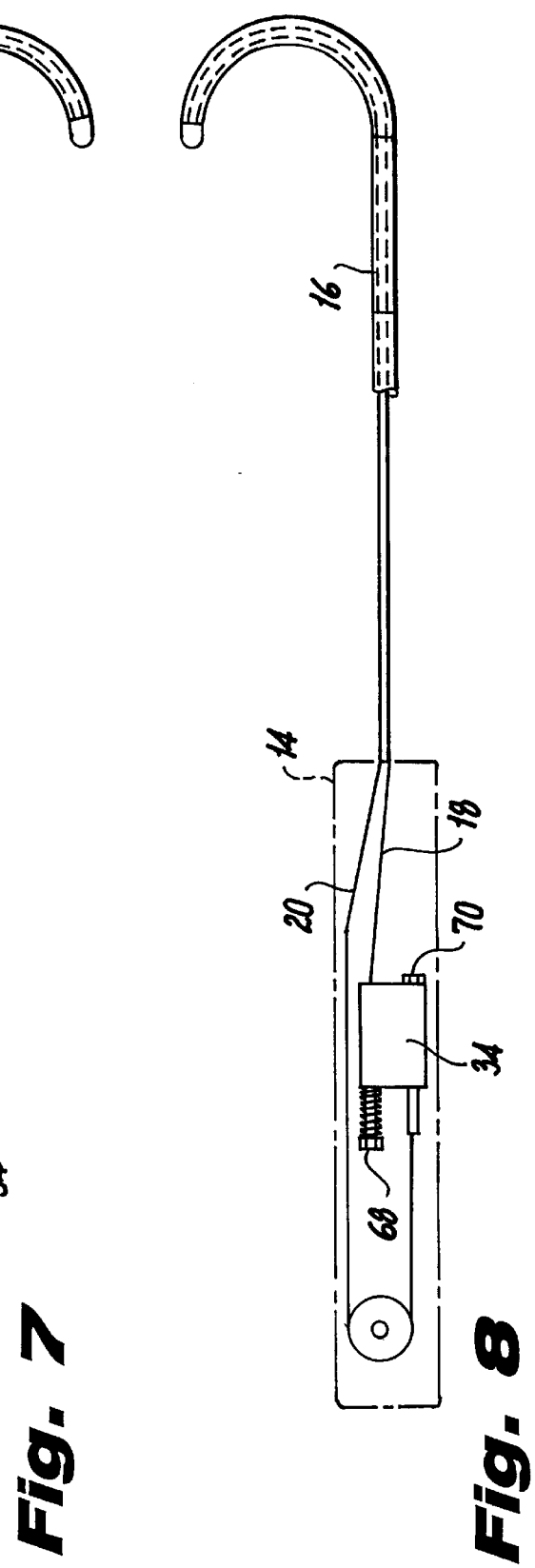

SLIDABLE CONTROL MECHANISM FOR STEERABLE CATHETER

FIELD OF THE INVENTION

The invention relates to the field of steerable catheters, and more particularly a slidable control mechanism for use with a steerable catheter to minimize control wire fatigue.

BACKGROUND OF THE INVENTION

Modern surgical procedures often necessitate localized diagnoses, or treatments applied to relatively inaccessible interior areas of the body. In the past, such procedures typically involved invasive surgery, enabling the physician to visually identify or treat the area of interest by accessing a relatively large opening or incision made in the body. Unfortunately, invasive surgical methods often include undesirable side-effects from the tissue trauma associated with the procedure. Often, the effects of the trauma prolong the healing and rehabilitation period for the patient.

To minimize the trauma often associated with invasive surgery, those skilled in the art have developed relatively small catheters for insertion into the vasculature of the body. Typically, the catheter accesses the body through a small incision made near the skin, where it can then be advanced to an area of interest. However, in order to navigate through the vasculature in a predictable manner, the catheter must be precisely controllable to position, as examples, ablation electrodes or imaging probes proximate specific tissues of interest.

To enable catheter manipulation inside the body, slidable control wire mechanisms are used to selectively "steer" the distal tip of the catheter while the operator inserts the device into the body. Such mechanisms typically include a pair of control wires that span the length of the catheter shaft, or body. The control wires have respective distal ends anchored to specific locations at the distal tip of the catheter body corresponding to predetermined deflectional movement. The proximal ends of the wires are mounted to a slider mechanism that responds to the operator to place one of the wires in tension, pulling at the catheter end for deflection in a first direction, while simultaneously compressing, or buckling, the other wire. An example of such a catheter configuration incorporating such a control mechanism may be found in U.S. Pat. No. 5,383,852, assigned to the assignee of the present invention.

While such devices generally provide a relatively high degree of directional deflection for the catheter tip, over a relatively short period of time the repetitive tensioning and buckling of the control wires often causes premature control wire fatigue. As a result, the operable lifespan of the device may be substantially shortened.

To address the problem of wire fatigue in a steerable medical device, one proposal (Takahashi U.S. Pat. No. 4,294,233) discloses steering the distal tip of an endoscope by independently manipulating two pull cables by turning an operating dial shaft. Means are provided for absorbing the slack, or buckled portion of the non-tensioned wire. The disclosed means include a long groove portion inside a slack absorbing member to define an escape area for the non-steered cable.

While this design may be satisfactory for its intended applications in the area of rotatable control mechanisms, it fails to address the slack absorption problem for slidable control mechanisms. Many operators prefer linearly displaceable sliding control mechanisms in particular applications. Moreover, the Takahashi design provides only a passive device to minimize compression on the non-selected cable.

Therefore, those skilled in the art have recognized the need for a slidable control mechanism for manipulating the distal end of a steerable catheter. Additionally, the need exists for a slidable control mechanism to actively assist in preventing compression on either steering cable. The control mechanism of the present invention satisfies these needs.

SUMMARY OF THE INVENTION

The control mechanism of the present invention extends the operable life of the control wires used in steering the distal tip of a steerable catheter. The life is prolonged by minimizing control wire fatigue resulting from compression or buckling of the wires during operation. A further advantage of the present invention involves the active assistance provided by a take-up mechanism to maintain a slight tension on a non-selected wire to ensure an anti-buckling effect.

To realize the advantages described above, the control mechanism of the present invention manipulates a pair of control wires having distal portions anchored to the distal end of a steerable catheter. The control wires extend longitudinally through the catheter and include proximal ends. The control mechanism includes a slider mechanism coupled to the proximal ends of the control wires and displaceable along a linear path to place a selected one of the wires in tension without placing the other of the wires in compression.

Other features and advantages of the present invention will be apparent from the following detailed description when read in conjunction with the accompanying drawings.

BRIEF DESCRIPTION OF THE DRAWINGS

FIG. 1 is a perspective view of a steerable catheter implementing a rotatable control mechanism according to one embodiment of the present invention;

FIG. 2 is a partial cross sectional view along line 2—2 of FIG. 1;

FIG. 3 is a diagrammatic illustration of the control mechanism in a neutral position;

FIGS. 4–5 are diagrammatic illustrations showing sliding actuation of the control mechanism; and FIGS. 6–8 are diagrammatic illustrations showing distal bending movement of the catheter distal end corresponding to the actuation of the control mechanism shown in FIGS. 3–5.

DETAILED DESCRIPTION OF THE INVENTION

Steerable catheters provide physicians, or operators, an indispensable tool for conveniently accessing the interior of the human body without the level of trauma commonly associated with more invasive surgical techniques. As shown by example in FIG. 1, a steerable catheter according to one embodiment of the present invention, and generally designated 12, includes an elongated hollow handle 14. The interior of the handle defines a compartment 15 (FIG. 2) for housing a control mechanism according to the present invention, generally designated 30. A longitudinal slot 17 formed along the side of the handle defines a linear path for slidable displacement of the control mechanism.

Further referring to FIG. 1, a narrow flexible shaft 16 projects longitudinally from one end of the handle for intravascular insertion. The shaft is typically formed from a polyurethane material of a predetermined stiffness and includes one or more longitudinally extending lumens (not shown) for running two or more steering or control wires 18 and 20 (FIGS. 3–5) therethrough.

To effect precision steering of the catheter distal end 16 during intravascular insertion, the control wires 18 and 20 run longitudinally through the catheter shaft lumen and respectively mount to specific distal points inside the shaft. The connection points correspond to predetermined directional deflections of the shaft in response to tensile forces placed on a selected wire. The steering wires may comprise stainless steel cables having tensile strengths of approximately 15.5 pounds.

Referring now to FIGS. 2 and 3, the control mechanism of the present invention 30 incorporates a slider mechanism 32 coupled to the proximal ends of the control wires 18 and 20 and displaceable along a linear path to place a selected one of said wires in tension without placing the other of said wires in compression.

The slider mechanism 32 includes a rectangularly formed slider control element 34 formed with a pair of spaced apart longitudinal passages 36 and 38 disposed in parallel relationship. Countersunk cavities 40 and 42 are formed in off-set opposite ends of the passages to define respective shoulders 44 and 46. A pair of spaced apart and longitudinally aligned support pins 48 and 50 (FIG. 2) project laterally from the side of the element and are complementally formed to slidably engage the handle slot 17. A thumb control 52 mounts to the pins to prevent the element from disengaging from the slot and responds to manually applied forces to actuate the control mechanism linearly along the slot path.

Referring to FIG. 3, a take-up device 60 is coupled to the slider mechanism via the control wires 18 and 20 to selectively secure the control wire proximal ends. The take-up device comprises a rotatable pulley 62 to redirect the force applied by the slider element 34 to the control wire 20, and a pair of biasing elements 68 and 70. The pulley includes a peripheral groove (not shown) and is rotatably carried by an axle 66 mounted rearwardly inside the handle compartment 15. The axle is positioned rearwardly of the slot 17, and oriented so that the pulley forms a pulley plane parallel to the path of the control wires 18 and 20.

The biasing elements 68 and 70 include respective shafts, or hypo-tubes, 72 and 74 slidably mounted within the passages 36 and 38. Tubes 72 and 74 include respective oversized-in-diameter stops 76 and 78 at the proximal ends of the tubes. The tubes are bonded to the proximal ends of the respective control wires 18 and 20 through a swaging operation performed during assembly of the control mechanism.

Further referring to FIG. 3, a particularly advantageous feature of the present invention involves an active anti-slacking function. To realize this capability, the biasing elements 68 and 70 include respective coil springs 80 and 82 slidably disposed externally of the respective hypo-tubes 72 and 74. The springs nest in the countersunk cavities 40 and 42 formed in the passages 36 and 38. When installed, the springs are confined in compression between the shoulders 44 and 46, and the shaft stops 76 and 78. The spring constants of the springs are of a level capable of exerting a slight tension on the wires to take up any slack, but below a level to cause any deflection of the catheter shaft.

Assembly of the control mechanism 30 comprises fairly straightforward techniques well known to those skilled in the art. Generally, with the respective control wires 18 and 20 already anchored to the distal end of the catheter shaft 16, the proximal ends of the wires are measured and trimmed to different lengths to accommodate the pulley 62. Accordingly, wire 20 is routed around the pulley groove and through the lower passage 38 formed in the slide element 34. The end of the wire is swaged to the hypo-tube shaft 74 with the coil spring 82 already disposed therealong. Wire 18 is then coupled to the slide element by routing through the upper passage 36 and swaging to the other hypo tube shaft 72.

Following initial assembly of the control mechanism to the control wires 18 and 20, calibration of the mechanism with respect to the desired directional deflections must be performed. Calibration methods are well known in the art, but generally involve setting the slider to a neutral position, approximately mid-way along the handle slot 17, and setting the control wires to a slight predetermined tension with the shaft in a substantially straight configuration, as illustrated in FIG. 6. Adjustment devices (not shown) provide correctable tensioning on the wires 18 and 20 to maintain a constant and relatively equivalent tension on each of the wires to define the neutral position. Once neutral has been established, as shown in FIGS. 3 and 6, the mechanism is linearly displaced to each of the extreme positions, as shown in FIGS. 4–5 and 7–8, with slight adjustments made as necessary to effect the proper deflections.

During operation, the catheter assembly 12 will normally be initially set to the calibrated relaxed or neutral configuration, such as that shown in FIGS. 3 and 6. Visual confirmation of the neutral state may be made by simply referring to the position of the thumb control 52, normally positioned midway along the slot 17. The catheter may then be directed into a relatively small incision formed in the vasculature to access the desired areas of interest.

Once inserted into the body, manipulation of the distal tip of the catheter may be effected by sliding the thumb control forwardly or rearwardly corresponding to the desired direction of deflection. Referring now to FIG. 4, an initial rearward force applied to the thumb control 52 linearly displaces the slider element 34 to rearwardly engage the upper hypo-tube stop 76. Continued rearward advancement of the slider element causes the hypo tube to pull the wire along the same direction, placing a tensile force on the wire and resulting in a directional deflection of the catheter shaft, as shown in FIGS. 4 and 7.

A particularly advantageous feature of the present invention is shown in FIGS. 4 and 5. With particular emphasis directed to FIG. 4, proximal movement of the slider element 34 is unimpeded by the lower hypo-tube 74 because the associated stop 78 is positioned at the distal end. In response to the sliding movement of the element 34 along the lower tube, the compressed coiled spring 82 nested within the lower passage cavity 42 expands as the distance between the shoulder 46 and stop 78 increases. The overall effect of the spring maintains a level of positive tension on the wire 20, preventing it from buckling or compressing as the other wire 18 deflects the catheter. Because buckling of the wire 20 is avoided, removing a common cause of premature control wire fatigue, the operational utility of the control wires will be substantially prolonged.

Slidable movement of the thumb control in the distal direction re-compresses the lower spring 82 into the cavity 42. Because the spring constant of the spring is lower than that required to exert a deflection on the catheter shaft, the hypo-tube 74 position remains relatively unchanged.

Simultaneously, the deflected catheter shaft 16 (from the proximal actuation of the thumb control) exerts an oppositely directed tensile force on the upper wire 18 sufficient to keep the upper spring 80 nested in the upper passage cavity 40 until the neutral position is reached. Continued distal actuation of the thumb element 52 then directs the slide element 34 distally to engage the lower hypo-tube stop 78 and place the wire 20 in tension sufficient to deflect the catheter tip. FIGS. 5 and 8 illustrate this action, with anti-slack results from the upper biasing element 68 similar to that discussed above for the biasing element 70.

While the control mechanism of the present invention has been described as the sole manipulation device for the catheter shaft, it will be understood that one or more additional control mechanisms may be implemented to complement the invention. For example, the capabilities of the present invention may be supplemented by a rotatable control mechanism 80 (FIG. 1) disposed proximate the thumb control 52 to effect steerable control over additional control wires routed through the shaft and anchored to the shaft distal end. A suitable rotatable control mechanism is disclosed in the applicant's co-pending application Ser. No. 08/818,353, assigned to the assignee of the present invention, and hereby incorporated by reference.

Those skilled in the art will appreciate the many benefits and advantages afforded by the control mechanism of the present invention. Of significant importance is capability of the slider mechanism to place a selected wire in tension to deflect the catheter shaft, without placing the other wire in compression. This prolongs the operational utility of the control wires by minimizing control wire fatigue due to repetitive buckling of the wires when slacked or compressed.

Moreover, the implementation of a take-up device to actively maintain a predetermined tension on each of the wires at all times further enhances the anti-slack capability of the slider mechanism.

While the invention has been particularly shown and described with reference to the preferred embodiments thereof, it will be understood by those skilled in the art that various changes in form and detail may be made therein without departing from the spirit and scope of the invention.

What is claimed is:

1. A control mechanism for manipulating a pair of control wires having distal portions respectively anchored to the distal end of a steerable catheter shaft corresponding to predetermined directional deflections of said catheter, said control wires extending longitudinally through said catheter and having respective proximal ends, said control mechanism including:
   a slider mechanism coupled to the proximal ends of said control wires and including a spring-biased take-up device coupled to said slider mechanism, said slider mechanism displaceable along a linear path to place a selected one of said wires in tension to deflect said distal end while taking up any slack in the other of said wires with said take-up device.

2. A control mechanism according to claim 1 wherein:
   said take-up device includes a pulley to rotatably carry one of said control wires; and
   said slider mechanism includes a slider control element disposed between said pulley and the catheter shaft to secure the proximal ends of said wires.

3. A control mechanism according to claim wherein:
   said take up device includes respective spring biasing elements to secure said control wire proximal ends and operative, as said slider mechanism moves a linear direction to place a selected one of said wires in tension, to maintain a predetermined tension on said cables to minimize buckling.

4. A control mechanism according to claim 3 wherein:
   said slider element is formed with a pair of spaced-apart passages disposed in parallel relationship relative to said wires, said passages having oppositely disposed cavities bounded interiorly by respective shoulders for seating said respective biasing elements; and
   said take-up mechanism includes
      respective stops affixed to the respective wire proximal ends in opposed parallel relationship, and
      respective bias elements slidably disposed in said cavities and confined in compression between said respective shoulders and said stops to form a predetermined tension on said wires in a neutral position, and operative, when said slider element advances along a selected direction to drive one of said stops in said direction and place a corresponding wire in tension, to expand the biasing element corresponding to the other of said stops and maintain said other stop in a substantially static state with said predetermined tension on said non-selected wire.

5. A control mechanism for manipulating a pair of control wires having distal portions respectively anchored to the distal end of a steerable catheter corresponding to predetermined directional deflections of said catheter, said control wires extending longitudinally through said catheter and having respective proximal ends, said control mechanism including:
   a slider mechanism coupled to the proximal ends of said control wires and having a control element displaceable along a linear path substantially parallel to said control wires, said slider mechanism including:
      a take-up device to secure said control wire proximal ends and operative, as said slider mechanism moves a selected linear direction to place a selected one of said wires in tension and deflect said catheter distal end, to take up the slack in the other of said wires.

6. A control mechanism according to claim 5 wherein:
   said take-up device includes a pulley to rotatably carry one of said control wires; and
   said slider mechanism includes a slider control element disposed between said pulley and the catheter shaft to secure the proximal ends of said wires.

7. A control mechanism according to claim 5 wherein:
   said take up device comprises a pair of spring biasing elements to secure said control wire proximal ends and operative, as said slider mechanism moves a linear direction to place a selected one of said wires in tension, to maintain a predetermined tension on said cables to minimize buckling.

8. A control mechanism according to claim 7 wherein:
   said slider control element is formed with a pair of spaced-apart passages disposed in parallel relationship relative to said wires, said passages having oppositely disposed cavities bounded interiorly by respective shoulders for seating said respective biasing elements; and
   said take-up mechanism includes
      respective stops affixed to the respective wire proximal ends
      respective bias elements slidably disposed in said cavities and confined in compression between said respective shoulders and said stops to form a predetermined tension on said wires in a neutral position, and operative, when said slider element advances along a selected direction to drive one of said stops in said direction and place a corresponding wire in tension, to expand the biasing element corresponding to the other of said stops and maintain said other stop in a substantially static state with said predetermined tension on said non-selected wire.

9. A steerable catheter for controllable manipulation through a vasculature, said catheter comprising:

a shaft having a distal end;

at least two control wires having distal portions respectively anchored to said shaft distal end and corresponding to predetermined directional deflections of said shaft; and a slidable control mechanism mounted upon the shaft, said slidable control mechanism including a slider mechanism coupled to the proximal ends of said control wires and including a spring-biased take-up device coupled to said slider mechanism, said slider mechanism displaceable along a linear path to place a selected one of said wires in tension to deflect said distal end while taking up any slack in the other of said wires with said take-up device.

10. A steerable catheter according to claim 9 wherein:

said take-up device includes a pulley to rotatably carry one of said control wires; and said slider mechanism includes a slider control element disposed between said pulley and the catheter shaft to secure the proximal ends of said wires.

11. A steerable catheter according to claim 10 wherein:

said take up device includes respective spring biasing elements to secure said control wire proximal ends and operative, as said slider mechanism moves a linear direction to place a selected one of said wires in tension, to maintain a predetermined tension on said cables to minimize buckling.

12. A steerable catheter according to claim 10 wherein:

said slider element is formed with a pair of spaced-apart passages disposed in parallel relationship relative to said wires, said passages having respective oppositely disposed cavities bounded interiorly by respective shoulders for seating said respective biasing elements; and said take-up mechanism includes respective stops affixed to the respective wire proximal ends in opposed parallel relationship, and respective bias elements slidably disposed in said cavities and confined in compression between said respective shoulders and said stops to form a predetermined tension on said wires in a neutral position, and operative, when said slider element advances along a selected direction to drive one of said stops in said direction and place a corresponding wire in tension, to expand the biasing element corresponding to the other of said stops and maintain said other stop in a substantially static state with said predetermined tension on said non-selected wire.

13. A steerable catheter according to claim 9 and further including:

a rotatable control mechanism including a driver rotatable about a central axis; and a deflection device coupled to said driver and comprising a pair of independently rotatable pulleys disposed coaxially on said central axis, said pulleys selectively responsive to directional rotation of said driver, as said driver rotates a selected radial direction, to place a selected one of said wires in tension while the other of said pulleys maintains said other of said wires in a static state thereby minimizing control wire fatigue.

14. A method of controlling a steerable catheter to minimize control wire fatigue, said catheter having a pair of control wires having distal portions anchored to the distal end of said catheter and proximal ends selectively secured to a control mechanism including a slider mechanism displaceable along a linear path, said method including the steps of:

applying tension to one of said control wires to deflect the distal end of said catheter by linearly displacing said slider mechanism; and taking up any slack in the other of said control wires to minimize control wire fatigue.

\* \* \* \* \*

UNITED STATES PATENT AND TRADEMARK OFFICE
Certificate

Patent No. 5,944,690            Patented: August 31, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gary S. Falwell, Manchester, NH; Sarkis Karakozian, Belmont, MA; and Jonathan M. Currier, Nashua, NH.

Signed and Sealed this Fifteenth Day of April 2003.

BRIAN L. CASLER
*Supervisory Patent Examiner*
Art Unit 3763